(12) United States Patent
Artal Soriano et al.

(10) Patent No.: US 11,051,692 B2
(45) Date of Patent: Jul. 6, 2021

(54) OPTICAL INSTRUMENT FOR MEASURING THE DENSITY OF THE MACULAR PIGMENT IN THE EYE AND ASSOCIATED METHOD

(71) Applicant: UNIVERSIDAD DE MURCIA, Murcia (ES)

(72) Inventors: Pablo Artal Soriano, Murcia (ES); Harilaos Ginis, Murcia (ES); Alexandros Pennos, Murcia (ES); Dimitrios Christaras, Murcia (ES)

(73) Assignee: UNIVERSIDAD DE MURCIA, Murcia (ES)

( * ) Notice: Subject to any disclaimer, the term of this patent is extended or adjusted under 35 U.S.C. 154(b) by 305 days.

(21) Appl. No.: 16/324,677

(22) PCT Filed: Jun. 16, 2017

(86) PCT No.: PCT/ES2017/070442
§ 371 (c)(1),
(2) Date: Feb. 11, 2019

(87) PCT Pub. No.: WO2018/007661
PCT Pub. Date: Jan. 11, 2018

(65) Prior Publication Data
US 2019/0298170 A1    Oct. 3, 2019

(30) Foreign Application Priority Data
Jul. 6, 2016  (ES) .................................. 201630921

(51) Int. Cl.
*A61B 3/12*    (2006.01)
*A61B 3/14*    (2006.01)
(Continued)

(52) U.S. Cl.
CPC .............. *A61B 3/12* (2013.01); *A61B 3/0008* (2013.01); *A61B 3/14* (2013.01)

(58) Field of Classification Search
CPC ....... A61B 3/12; A61B 3/0008; A61B 3/0025; A61B 3/10; A61B 3/1225; A61B 3/14
See application file for complete search history.

(56) References Cited

U.S. PATENT DOCUMENTS 6,315,412 B1 *  11/2001  Snodderly ................ A61B 3/02
                                                        351/200
2009/0153798 A1 *  6/2009  Dick .................... A61B 5/0261
                                                        351/206
(Continued)

FOREIGN PATENT DOCUMENTS

DE  102007047300 A1   0/2009
EP      2668894 A1    12/2013
WO   2015/035175 A1   3/2015

OTHER PUBLICATIONS

International Search Report of corresponding PCT application No. PCT/ES2017/070442 including English Translation.
(Continued)

*Primary Examiner* — Jordan M Schwartz
(74) *Attorney, Agent, or Firm* — Ladas & Parry LLP

(57) ABSTRACT

Optical instrument for measuring the density of macular pigment in the eye and associated method. The instrument includes: a light source (500), several lenses L1, L2, L3 between the light source and the eye, a diaphragm D1 conjugate to the eye pupil plane, a photodetector (520), a mirror M that directs the light exiting the eye to the photodetector (520), a diaphragm D2 conjugated to the pupil plane of the eye, at least one lens L4 between diaphragm D2 and the photodetector (520), the light source (500) has a central part (501) and a peripheral part (502), the light source (500) being modulated at four different frequencies
(Continued)

corresponding to green light in the central part and in the peripheral part, blue light in the central part and in the peripheral part, projecting the light from the light source (500) on the fundus of the eye.

11 Claims, 5 Drawing Sheets

(51) Int. Cl.
*A61B 3/10* (2006.01)
*A61B 3/00* (2006.01)

(56) References Cited

U.S. PATENT DOCUMENTS

| | | |
|---|---|---|
| 2012/0008093 A1 | 1/2012 | Spaide |
| 2013/0321764 A1* | 12/2013 | O'Brien .................. A61B 3/12 351/206 |
| 2014/0118698 A1 | 5/2014 | Gierhart et al. |

OTHER PUBLICATIONS

Written Opinion of the corresponding PCT application No. PCT/ES2017/070442 including English Translation.

* cited by examiner

OPTICAL INSTRUMENT FOR MEASURING THE DENSITY OF THE MACULAR PIGMENT IN THE EYE AND ASSOCIATED METHOD

RELATED APPLICATION

This application is a national phase entry under 35 USC 371 of International Patent Application No.: PCT/ES2017/070442 filed on 16 Jun. 2017, which claims priority from Spanish Application No.: 201630921 filed on Jul. 6, 2016 the entire contents of which are incorporated herein by reference.

FIELD OF THE INVENTION

The present invention refers to an optical instrument and an associated method for measuring the density of the macular pigment in the eye, and more specifically in the human eye, and falls within the field of ophthalmic systems and ophthalmology.

BACKGROUND OF THE INVENTION

The macular pigment is found in the macula of the human eye, the part of the retina associated with vision's highest resolution (see, e.g., D. M, Snodderly, P K Brown, F C Delori, and J D Auran, "The macular pigment.I. Absorbance spectra, localization, and discriminafion from other yellow pigments in primate you refine," Investig. Ophthalmol. Vis. Sel., vol. 25, no. 6, pp. 660-673, 1984).

The Macular Pigment is of dietary origin, and hence, the amount of pigment is related to the individual's diet. It is believed that higher optical density is related to better retinal health. It is proposed that higher density of the pigment may have a protective role against retinal diseases such as macular degeneration. Studies have shown that the macular pigmentation can play an important role in preventing eye diseases and improvement of visual function (see, for example, L T Sharpe, A. Stockman, H. Knau, and H. Jagle, "Macular pigment derived from plant densities and peripheral spectral sensitivity differences", Vision res, vol 38, no 21, pp 3233-3239, 1998; and P V Algvere, J, and S. Seregard Marshall, "Age-related maculopathy and the impact of blue light hazard," Acta Ophthalmol. Scand., vol. 84, no. 1, pp. 4-15, 2006).

Age-related macular degeneration (AMD) is one of the leading causes of blindness in Western countries. Due to the lack of a fully effective treatment, prevention is of great importance. There is growing evidence that nutritional intervention may reduce the incidence of macular degeneration, or at least reduce its progression.

In particular, modification of dietary intake or food supplements may lead to an increase of specific carotenoids in the retina (lutein (L) and zeaxanthin Z) that comprise the macular pigment (MP). When such supplements are administered, monitoring the optical density of the macular pigment density (MPD or MPOD) are of great importance.

To date, the instruments capable of measuring the density of the macular pigment are either subjective based on psychophysical methods, such as heterochromatic flicker photometry (HPF), or high-end devices which capture images of the retina at two wavelengths. In these instruments, the macular pigment density is calculated from the relative absorption of the blue spectrum which is characteristic of the absorption spectrum of the macular pigment.

The area of a human eye where the macular pigment is located has a characteristic absorption spectrum, which can be seen in FIG. 1 (see, for example, L. Gao, R T Smith, and T S Tkaczyk, "hyperspectral camera retinal With the Snapshot Image Mapping Spectrometer (IMS)," Biomed. Opt. Express, vol. 3, no. 1, p. 48, 2012).

Psychophysical devices have been used for over three decades in the measurement of macular pigment density (see, for example, R A Bone and J M B Sparrock, "Comparison of macular pigment densities in human eyes," Vision Res., Vol. 1 January, 10, pp 1057-1064, 1971; B R Hammond, Johnson E J. Russell R M. Krinsky N I, K J Yeum, Edwards and D M R B Snodderly, "Dietary modification of human macular pigment density," Investig Ophthalmol. Vis Sci, vol 38, No. 9, pp 1795-1801, 1997; and J S Werner, R. Donnelly and S K Kliegi, "Aging and human macular pigment density Appended With translations from the work of Max Schuitze and Ewald Hering," Vision res., vol. 27, no. 2, pp. 257-268, 1987). There are several commercial devices based on heterochromatic flicker photometry (HFP), such as the MPSII (Elektron Technology, Cambridge, UK), which are well established in the clinical assessment of MPOD. However, they have a serious limitation due to the very nature of the subjective method that is not always comprehensible by the patient and can provide inconsistent results.

Optical methods are based on comparative analysis of two images of the fundus of the eye at blue and green. The intensity images is proportional to the reflectance of the fundus of the eye at those wavelengths. Given that most of the light is reflected from layers located posterior to the macular pigment is, changes in reflectance are attributed to the absorption of the macular pigment.

The procedure for determining the density of the macular pigment from the relative intensities can be found in the literature (see, for example, F C Delori, D G Goger, B R Hammond, D M Snodderly and S A Burns, "Macular pigment density measured by autofluorescence spectrometry: comparison with reflectometry and heterochromatic flicker photometry" J. Opt. Soc. Am. A, vol. 18, no. 6, pp. 1212-1230, 2001). This document shows the application of the Fundus Reflectometry an imaging system. Two recorded at different wavelengths (blue and green) images examined by comparison to derive the difference in reflectance of the fundus of the eye. The macular pigment density can be calculated from reflectance data using an appropriate formula.

Optical methods are objective, unlike psychophysical method which are subjective; however they require more expensive components (such as highly sensitive cameras) and/or electro-optical elements such scanning systems and require non-trivial image processing. Moreover, measurements with these systems may have errors associated with ambient light.

Based on the above, there is a need for a new optical technique for measuring the density of the macular pigment which is more practical, compact, and robust repetitive.

SUMMARY OF THE INVENTION

The object of the present invention is to provide an optical instrument and a corresponding method for measuring the density of the macular pigment in the eye that deals with the aforementioned drawbacks.

The present invention provides an optical instrument for measuring the density of the macular pigment in the eye which comprises:

a light source, several lenses L1, L2, L3 located between the light source and the eye to be studied, a diaphragm D1 conjugate to the pupil plane of the eye to be studied to allow control of the position of entrance of the light in the eye, a photodetector, a mirror M that directs the light exiting the eye to the photodetector, a diaphragm D2 conjugate to the pupil plane, which determines the output path of the light from the fundus of the eye, at least one lens L4 between diaphragm D2 and the photodetector, wherein the light source comprises a central part and a peripheral part, the light source being modulated at four different frequencies corresponding to green light in the central part, green light in the peripheral part, blue light in the central part and blue light in the peripheral part, projecting the light source on the fundus of the eye, so that the central part of the light source is projected onto the macula of the eye, and the response signal from the fundus of the eye is received at the photodetector.

The invention also provides a method for measuring the density of the macular pigment in the eye employing an instrument of the invention and comprising the following steps:

Simultaneous projection on the fundus of the eye of the modulated light at four different frequencies corresponding to green light in the central part, green light in the peripheral part, blue light in the central part and blue light in the peripheral part, using the light source.

Collecting the response signal of the fundus of the eye in the photodetector.

The signal collected by the photodetector is subjected to a temporal Fourier analysis that provides the light amplitude for each frequency, allowing the differentiation of the components of each color and the spatial localization in the retina.

Calculation of macular pigment density from the relative reduction of the reflectance in blue between the periphery and the macula.

The present invention therefore provides an optical instrument for measuring the density of the macular pigment that is objective, fast, compact and robust, and an associated method. The instrument does not depend on subjective responses of each subject, since it directly measures the optical density of the macular pigment (objectively) and not through its visual effects on the subject of measurement (subjectively).

BRIEF DESCRIPTION OF THE DRAWINGS

Below is illustrated in a non-limiting manner the object of the present invention with reference to the accompanying drawings in which.

DETAILED DESCRIPTION OF THE INVENTION

Figure 1:
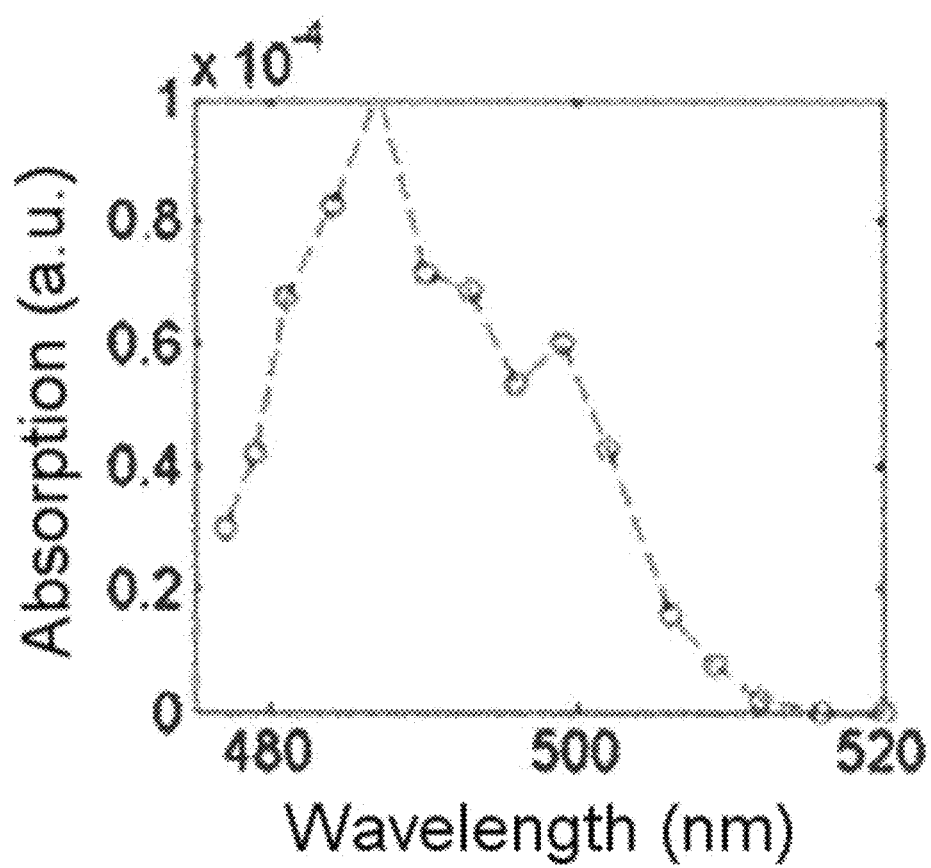
FIG. 1 shows the characteristic absorption spectrum of the macular pigment of macular area of a human eye, as found in prior art.

FIG. 1 shows a graph of the characteristic absorption spectrum of the macular pigment of the macular area of a human eye.

Figure 2:
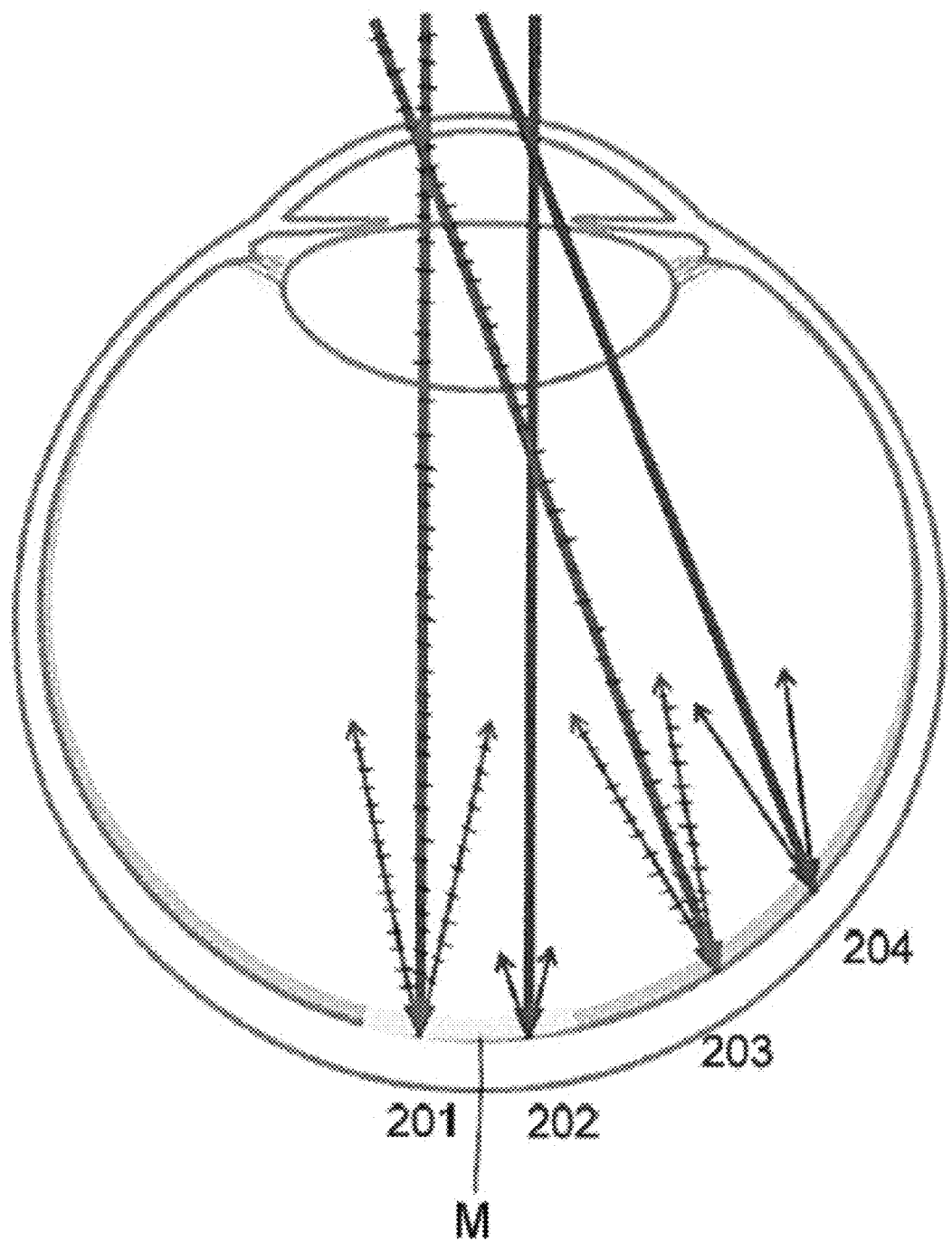
FIG. 2 shows the principle of fundus reflectometry, used in prior art.

FIG. 2 shows schematically a section of a human eye, where the light reflected from the macula M is attenuated due to the presence of macular pigment. In this figure (from prior art) blue light is depicted in continuous lines and green light in dotted lines. The relative reduction in blue reflectance (between the periphery 204 and the macula 202), using green light as reference (macular pigment affects insignificantly green light; periphery 203 and macula 201), can be used to calculate the macular pigment density.

Figure 3:
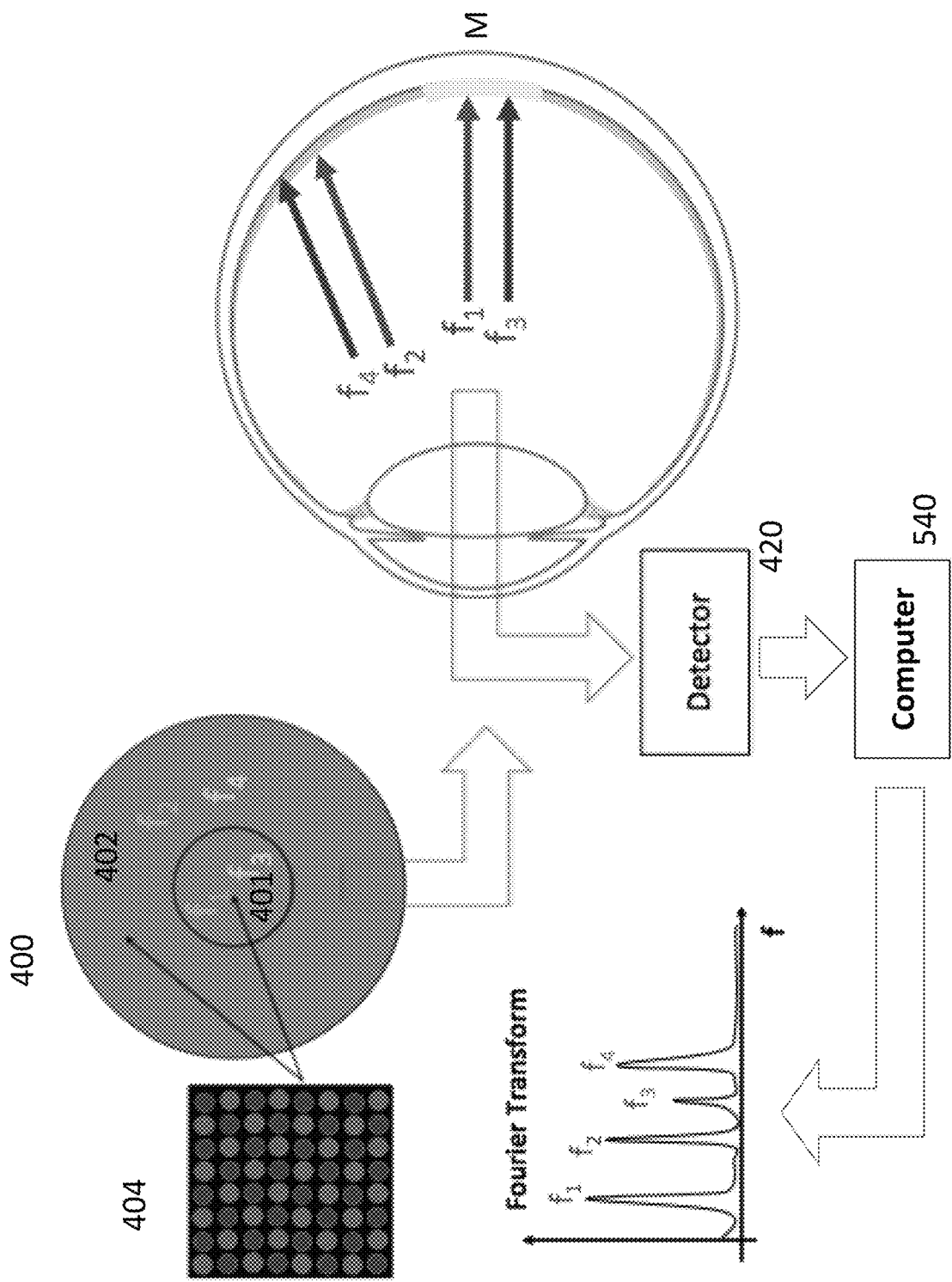
FIG. 3 shows the principle of fundus reflectometry applied in the Fourier domain.

FIG. 3 shows the principle of fundus reflectometry applied in the Fourier domain. A light source 400 comprising of a central part 401 and peripheral part 402 is projected onto the fundus of the human eye so that the central part 401 is projected onto the macular area M. The light source 400 consists of two sources 404, a green one and a blue one, both distributed in the central part 401 and peripheral part 402 of source 400.

The light sources are modulated at four different frequencies f1, f2, f3 and f4, corresponding to the green center, green periphery, blue center and blue periphery respectively. The response signal from the fundus is collected by the photodetector 420. The Fourier analysis reveals the amplitude for each frequency. Knowing which frequency corresponds to each wavelength and location (center or periphery) the macular pigment density can be calculated as described above.

Modulation frequencies are in a range between 100 Hz and 100000 Hz.

Figure 4:
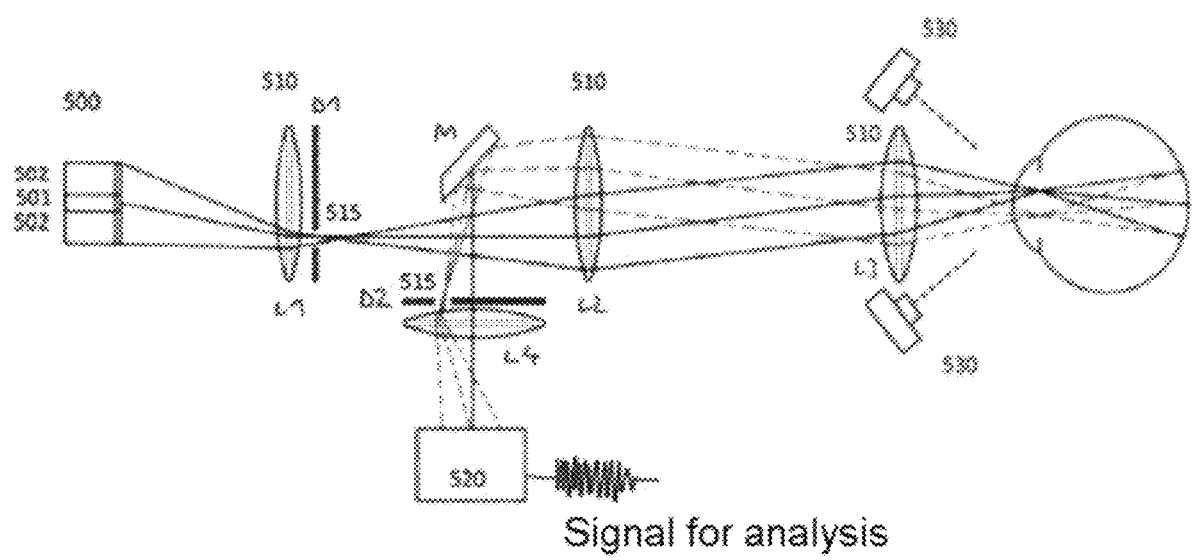
FIG. 4 shows a diagram of the optical instrument of the invention for the projection of light on the fundus of the eye and the recording the reflected signal by the photodetector.

FIG. 4 shows the optical arrangement of the invention, for the projection of the source on the fundus and the capture of the reflected signal. A light source 500 has a central part 501 and peripheral part 502. A combination of lenses 510 and diaphragms 515 are used to project the light source on the fundus such that the central part 501 is projected onto the macula. The light source 500 is modulated into four different frequencies corresponding to the green center, green periphery, blue center and blue periphery. The response signal from the fundus is received by the detector 520. The Fourier analysis reveals the amplitude of each frequency. Knowing which frequency corresponds to which wavelength and retinal location (center or periphery) one can calculate the macular pigment density. One or more cameras 530 are used for the alignment of the eye under investigation.

Figure 5:
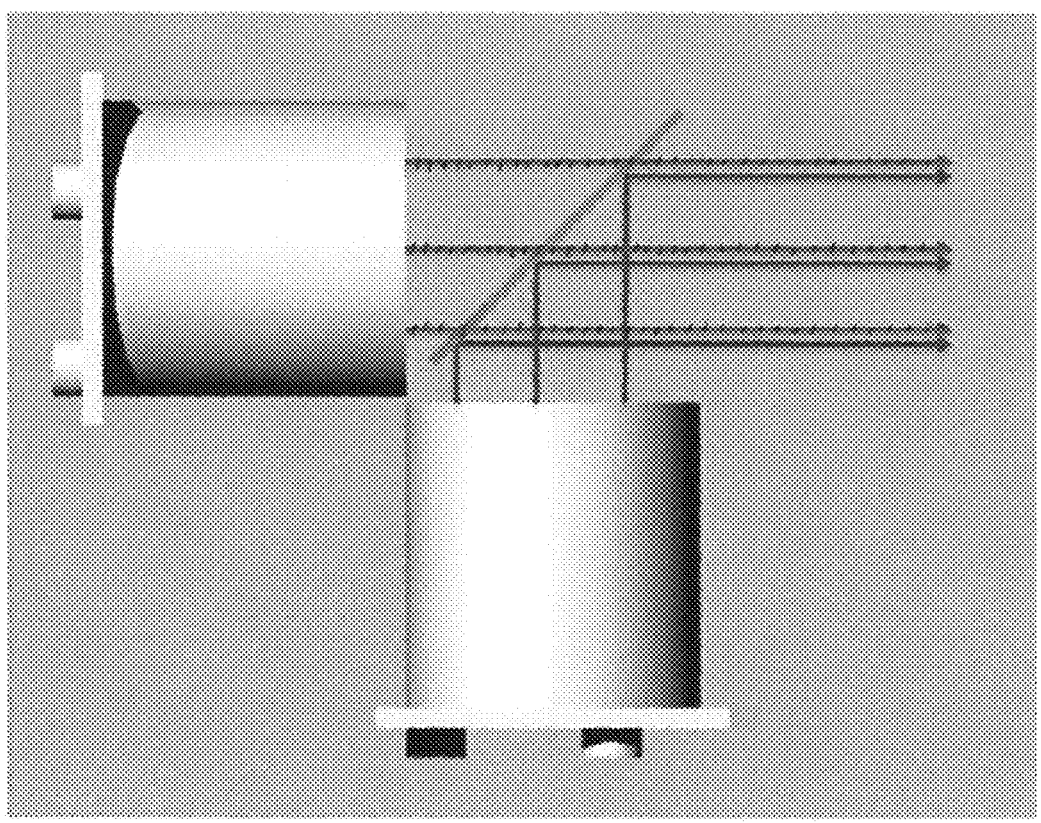
FIG. 5 shows a schematic of a light source comprising of two separate light sources, each one emitting at a different wavelength.

FIG. 5 shows a possible construction of a light source comprising of two separate light sources (each characterized by a central and a peripheral part) where the two sources have the desired wavelengths (blue and green) and the two sources are combined with a suitable dichroic mirror that allows the transmission of the green wavelength while reflecting the blue wavelength. Blue light is depicted with continuous lines and green light with dotted lines.

According to one embodiment, the light source consists of a central part and a peripheral part, distributed in a ring arrangement. The light source is modulated in four different frequencies corresponding to the center (green), periphery (green), center (blue) and periphery (blue). In one preferred embodiment, the wavelength of blue light is between 440 nm and 490 nm and is produced by Light Emitting Diodes (LED); also, the wavelength of the green light is between 530 nm and 580 nm and is emitted by different LEDs. The central and peripheral parts of the light source have concentric opaque walls separating the green light and blue light LEDs that they are projected in both the central part and the peripheral part of the source. The appropriate electronics allow the control of each LED group separately to the desired modulation frequency. An appropriate combination of lenses and diaphragms form images of the light source of LEDs on the retina. The light source is projected onto the fundus such that the central part is projected on the macula (central fovea). This is accomplished by asking the subject to look at the center of the source using a fixation stimulus.

A telescopic system conjugates optically a diaphragm D1 to the desired area of the pupil of the eye. In addition, a second diaphragm D2 is placed in front of detector 520 conjugated to a different part of the pupil. Thus, the light reaching the detector 520 is light originated solely from the fundus, eliminating reflected light in other ocular media, particularly the cornea.

Light reflected from the fundus is recorded by photodetector 520. A Fourier analysis performed on a computer 540 provides the light intensity for each frequency. Knowing which frequency corresponds to which wavelength and retinal location (center or periphery), the macular pigment density is calculated. One or more additional cameras 530 may be used for alignment of the eye during the measurement.

Although specific embodiments of the invention have been described and illustrated, it is evident that modifications may be introduced within its scope, and should not be limited to said embodiments but only to the content of the following claims.

The invention claimed is:

1. An optical instrument for measuring and recording response signals from an eye of a subject that can be used to determine the density of macular pigment in the eye, the eye comprising a fundus with a macular area and a peripheral area, the light optical instrument comprising:
   (a) at least one light source comprising a central part and a peripheral part, the at least one light source emitting light that is modulated at four different frequencies f1, f2, f3 and f4 corresponding to a first green light emitted from the central part at modulated frequency f1; a second green light emitted from the peripheral part at modulated frequency f2, a first blue light emitted from the central part at modulated frequency f3 and a second blue light emitted from the peripheral part at modulated frequency f4;
   (b) first means for controlling a path of the light emitted from the at least one light source so that the first green light and the first blue light emitted from the central part of the at least one light source is directed onto the macular area of the eye and simultaneously the second green light and the second blue light emitted from the peripheral part of the at least one light source is directed onto the peripheral area of the eye, the first means comprising a plurality of lenses disposed between the at least one light source and the eye and a first diaphragm conjugated to a pupil plane of the eye;
   (c) a photodetector for receiving the light emitted from the at least one light source that is reflected from the macular and peripheral areas and for recording data relative thereto; and
   (d) second means for directing light reflected from the macular and peripheral areas to the photodetector and for eliminating light reflected from ocular areas of the eye other than the macular and the peripheral areas, the second means comprising a mirror, a second diaphragm conjugated to the pupil plane of the eye and at least one lens disposed between the second diaphragm and the photodetector.

2. The optical instrument according to claim 1, wherein the central part and the peripheral part of the at least one light source are configured with the peripheral part having a ring shape surrounding the central part.

3. The optical instrument according to claim 1, wherein the light emitted by the at least one light source is produced by respective green and blue light emitting diodes.

4. The optical instrument according to claim 1, wherein the first blue light and second blue light have respective wavelengths between 440 nm and 490 nm and the first green light and second green light have respective wavelengths between 530 nm and 580 nm.

5. The optical instrument according to claim 3, wherein the at least one light source comprises opaque concentric walls disposed in the central part and peripheral part respectively that separate the green light emitting diodes from the blue light emitting diodes.

6. The optical instrument according to claim 1, further comprising at least one camera.

7. The optical instrument according to claim 1, wherein the at least one light source comprises a first light source and a second light source that are separate from each other, the first light source emitting green light and the second light source emitting blue light, each of the first and second light sources having a central part and a peripheral part, the optical instrument comprising a dichroic mirror disposed with respect to the first and second light sources to transmit the green light emitted from the first light source and to reflect the blue light emitted from the second light source.

8. The optical instrument according to claim 1, wherein the modulation frequencies f1, f2, f3, and f4 are in a range between 100 Hz and 100000 Hz.

9. The optical instrument according to claim 1, further comprising means for analysing the data recorded by the photodetector and for calculating the density of the macular pigment of the eye based on a relative intensity of each of the frequencies f1, f2, f3 and f4 received by the photodetector.

10. A method for measurement of macular pigment density in an eye of a subject, the eye comprising a fundus with a macular area and a peripheral area, the method comprising the steps of:
   (a) providing the optical instrument of claim 1;
   (b) simultaneously projecting, using the optical instrument, modulated light at the four different frequencies f1, f2, f3 and f4 onto the eye of the subject so that the first green light and the first blue light emitted from the central part of the at least one light source is directed onto the macular area of the fundus of the eye and the second green light and the second blue light emitted from the peripheral part of the at least one light source is directed onto the peripheral area of the fundus of the eye;
   (c) collecting a response signal from the fundus of the eye in the photodetector of the optical instrument;
   (d) subjecting the response signal to a temporal Fourier analysis that provides a light amplitude for each of the frequencies f1, f2, f3 and f4; and
   (e) calculating a macular pigment density of the eye from a relative reduction of reflectance in the first and second blue, lights between the peripheral area and the macular area of the fundus of the eye.

11. The method according to claim 10, comprising aligning the optical instrument with the eye with a camera prior to step (a).

\* \* \* \* \*